US007045681B2

(12) United States Patent
Rodriguez et al.

(10) Patent No.: US 7,045,681 B2
(45) Date of Patent: May 16, 2006

(54) DNA SEQUENCES CAPABLE OF EXPRESSING FOREIGN PROTEINS AND METABOLITES IN DICOTYLEDONOUS PLANTS AND CELL CULTURE

(75) Inventors: Raymond L. Rodriguez, Davis, CA (US); Bruce R. Thomas, Davis, CA (US)

(73) Assignee: The Regents of the University of California, Oakland, CA (US)

(*) Notice: Subject to any disclaimer, the term of this patent is extended or adjusted under 35 U.S.C. 154(b) by 423 days.

(21) Appl. No.: 10/274,748

(22) Filed: Oct. 18, 2002
(Under 37 CFR 1.47)

(65) Prior Publication Data
US 2004/0077040 A1    Apr. 22, 2004

(51) Int. Cl.
*C12N 15/82* (2006.01)
*C12N 15/90* (2006.01)
*C12N 15/29* (2006.01)

(52) U.S. Cl. .................... 800/278; 800/320.2; 800/317
(58) Field of Classification Search ............... 536/23.1; 800/295, 278, 320, 317; 435/320
See application file for complete search history.

(56) References Cited

U.S. PATENT DOCUMENTS

| 5,460,952 A | 10/1995 | Yu et al. ............ 435/69.1 |
| 5,888,789 A | 3/1999 | Rodriguez ............ 435/468 |
| 6,048,973 A | 4/2000 | Rodriguez ............ 536/24.1 |

OTHER PUBLICATIONS

M. T. Chan et al., (1994) "Novel Gene Expression System for Plant Cells Based on Induction of α-Amylase Promoter by Carboydrate Starvation" The Journal of Biological Chemistry, vol. 268 (# 26), pp. 17635-17641.
B. Li et al., (1992) "Characterization and Subcellar Localization of Debranching Enzyme and Endoamylase from Leaves of Sugar Beet" Plant Physiology, vol. 98, pp. 1277-1248.
B.R. Thomas et al. (1994), "Metabolite Signals Regulate Gene Expression and Source/Sink Relations in Cereal Seedlings" Plant Physiol., vol. 106, pp. 1235-1239.
D. Yamanuchi et al. (1990), "Nucleotide sequence of cDNA for α-amylase from cotyledons of germinating *Vigna mungo* seeds" Nucleic Acids Res., vol. 18 (# 14), p. 4250.
D.M. Lawrence et al. (1990), "Mobilisation of storage reserves during germination and early seedling growth of sugar beet" Physiologia Plantarium, vol. 78, pp. 421-429.
J.W. Kim et al. (1997), "Expression of α-Amylase in Cultured Callus of French Bean" J. Plant Res., vol. 110, pp. 357-361.
H. Takeuchi et al. (1993), "Nucleotide Sequence of the α-Amylase Gene from *Vigna mungo*" Plant Physiol. (Plant Gene Register), vol. 103, p. 1459.
N. Huang et al.(1990), "Classification and characterization of the rice α-amylase multigene family" Plant Molecular Biology, vol. 14, p. 665-668.
N. Huang et al. (1990), "Structural organization and differential expression of rice α-amlase genes" Nucleic Acids Res., vol. 18 (#23), p. 7007-7014.
X. Ye (Jan. 14, 2000), "Engineering the Provitamin A (β-Carotene Biosynthetic Pathway into (Carotenoid-Free) Rice Endosperm" Science, vol. 287, p. 303-5.

*Primary Examiner*—Ashwin Mehta
*Assistant Examiner*—Barba M. Koroma
(74) *Attorney, Agent, or Firm*—Townsend and Townsend and Crew LLP

(57) ABSTRACT

The present invention relates to a method for producing a gene product by expressing a gene encoding said gene product in angiosperm host cells, which method comprises: a) constructing a vector expressible in angiosperm host cells, said vector comprising a promoter region derived from an amylase gene selected from SBAmyA, SBAmyB, SBAmyC genes or SBAmyD of the sugar beet and a gene encoding a desired gene product; b) transforming a compatible angiosperm host cell with said vector; c) cultivating the resulting transformant host cell to a sugar-depleted or sugar-free condition to promote the expression of said gene under the control of such promoter region; and d) recovering the product of the expressed gene. The sugar beet gene when incorporated into a dicot seed or plant has improved biological properties. The gene sequences and the products thereof are claimed.

10 Claims, 15 Drawing Sheets

Gamma Component of Virus nd18g seg and BSU 13917

Window Size = 30  Strand = Both  Scoring Matrix: DNA Database
Min. % Score = 100  Jump = 1  Matrix
Hash Value = 6

Non overlaping sequences
nd18gseg  0 ———▶ 15
bsu13917  0 ———▶ 15

BSU13917 (y-axis: 5 to 50)
x-axis: GTATAGCTTGAGCATTACCGTCGTGTAATTGCAACACTTGGCTT
nd18g seq
mv

FIG._1

Gamma component of virus nd18g seg and BSU 35767

Window Size = 30  Strand = Both  Scoring Matrix: DNA Database
Min. % Score = 100  Jump = 1  Matrix
Hash Value = 6

BSU35767 (y-axis: 3760 to 3785)

Non overlaping sequences
nd18gseg  2777 ———▶ 2790
bsu35767  2777 ———▶ 2790 x-axis: CTCAGCTTCGGTCCCCCAAGGGAAGACCA
nd18g seq
mv

FIG._2

Restriction Enzyme Analysis of BSU13917

500　　　1000　　　1500　　　2000　　　2500

BSU13917 = BSMV gamma segment

*FIG._3*

Restriction Enzyme Analysis of BSU13917

Pst1, EcoR5, Xho1, Xho1, EcoR5, Cla1, Kpn1, Sph1, Hind3

*FIG._4*

Restriction Enzyme Analysis of BSU35767

500　　1000　　1500　　2000　　2500　　3000　　3500

BSU35767 = BSMV gamma segment

*FIG._5A*

Restriction Enzyme Analysis of BSU35767

Sph1, Cla1, EcoR5, BamH1, Xho1, EcoR1, Kpn1, Hind3, Kpn1, EcoR5

*FIG._5B*

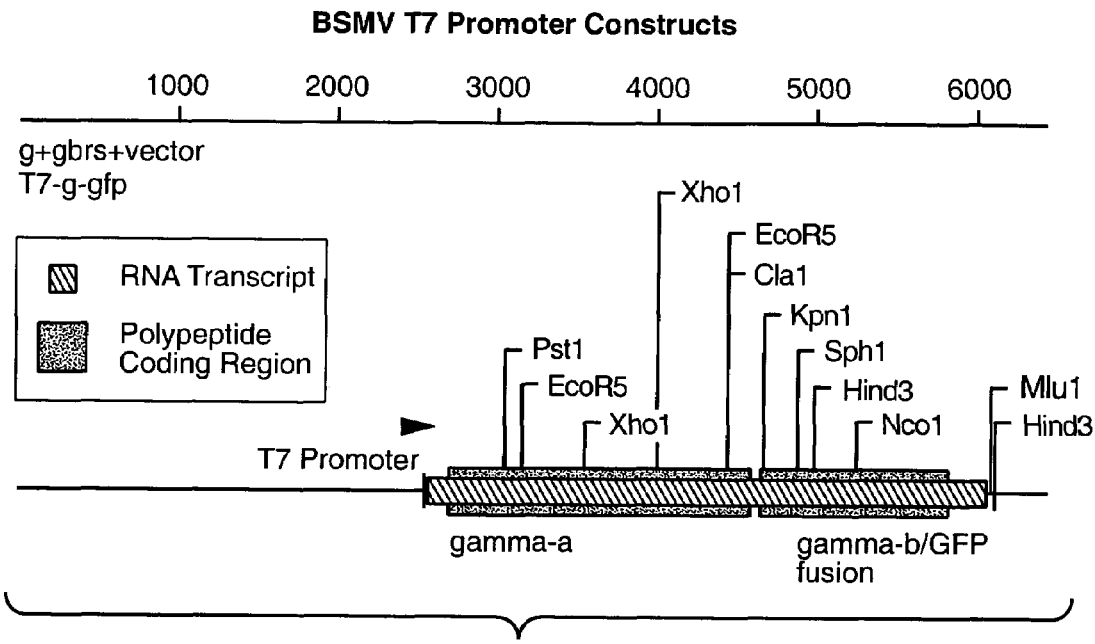
FIG._6A
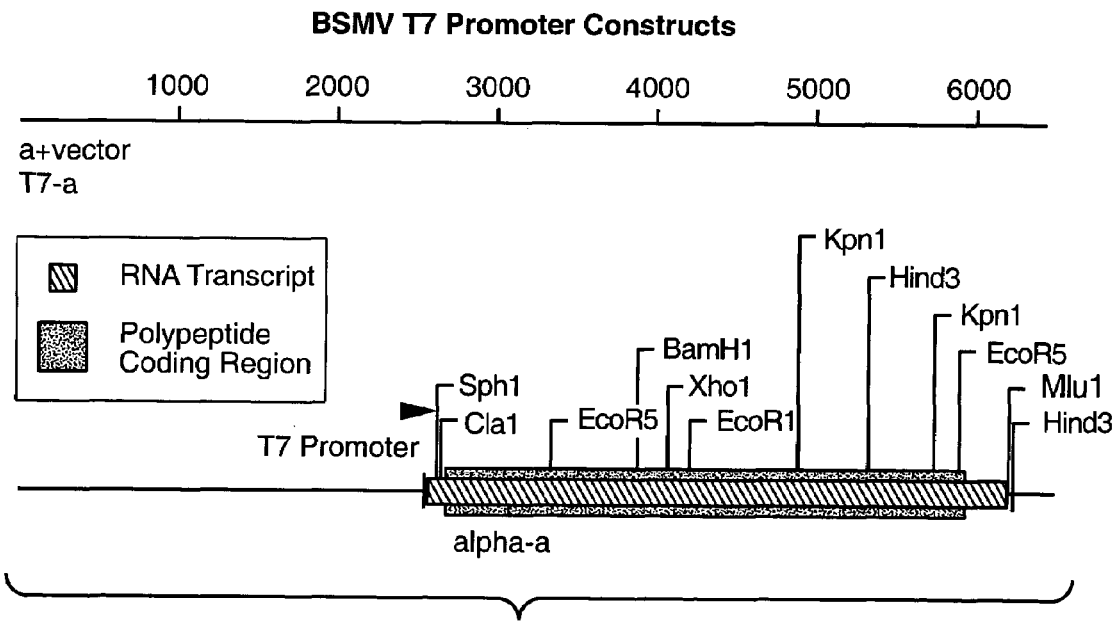
FIG._6B

α-Amylas Gen Summary.
Sugar Beet α-amylase Gene Phylogeny.

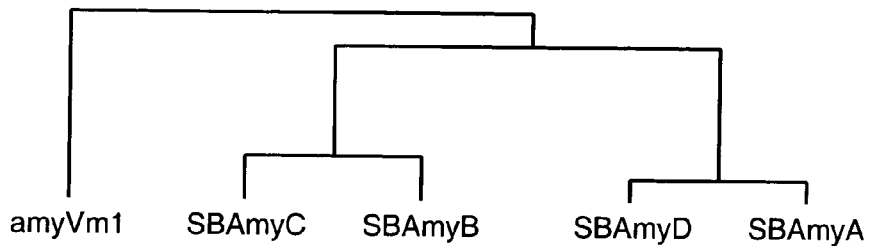

FIG._7A

α-Amylase Gene Summary.
Sugar Beet α-amylase Gene Expression.

| Gene Expression | SBAmyC | SBAmyB | SBAmyD | SBAmyA |
|---|---|---|---|---|
| Seedlings | ++++ | ++ | - | - |
| Cell Culture | - | - | ++ | ++++ |
|  | pH 4.5?<br>isozyme? | pH6.5?<br>isozyme? |  |  |

FIG._7B

α-Amylase Gene Summary.
Sugar Beet α-amylase Genomic Clone Isolation.

| Genomic Clone | SBAmyC | SBAmyB | SBAmyD | SBAmyA |
|---|---|---|---|---|
| Clone Number | # 48<br># 7 | #11 | NA | NA |

FIG._7C

SBAmyB Gene - Restriction Maps.

The SBAmyB gene was subcloned as two plasmid inserts. These contain all of the 5' flanking region that is available in the lambda clone.

λSB#11 in EMBL3 SP6 /T7

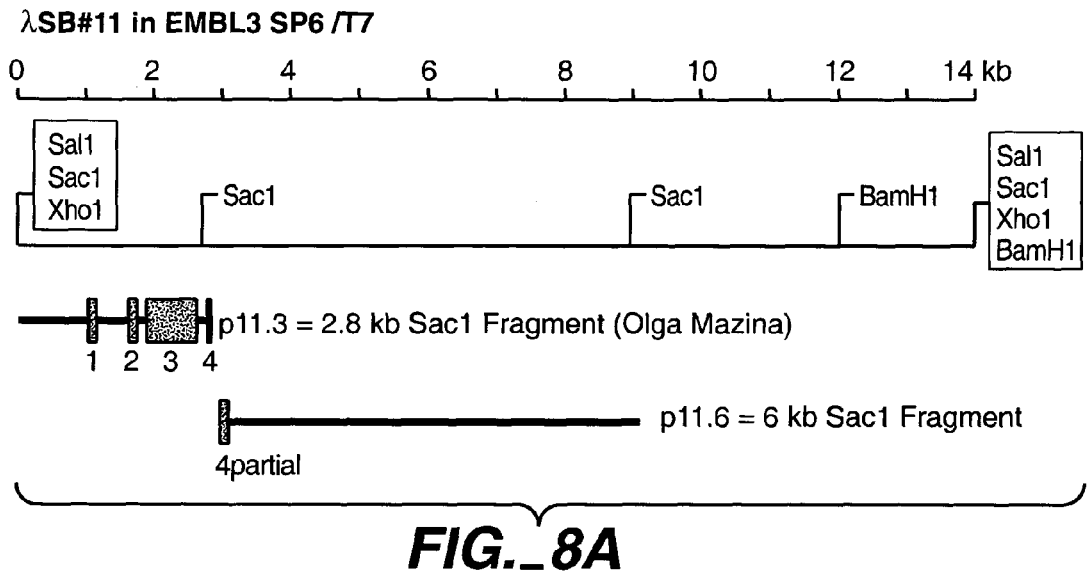

FIG._8A

SBAmyB Gene - Restriction Maps.

The SBAmyB gene was subcloned as two plasmid inserts. These contain all of the 5' flanking region that is available in the lambda clone.

p11.3 = 2.8 kb Sac1 Fragment from SB#11
in pUC19

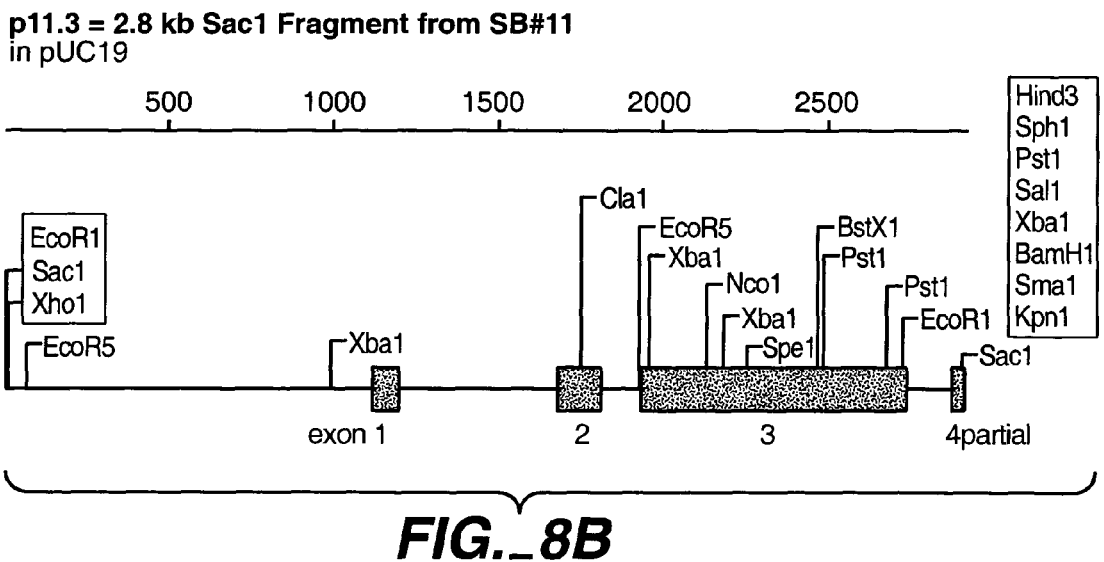

FIG._8B

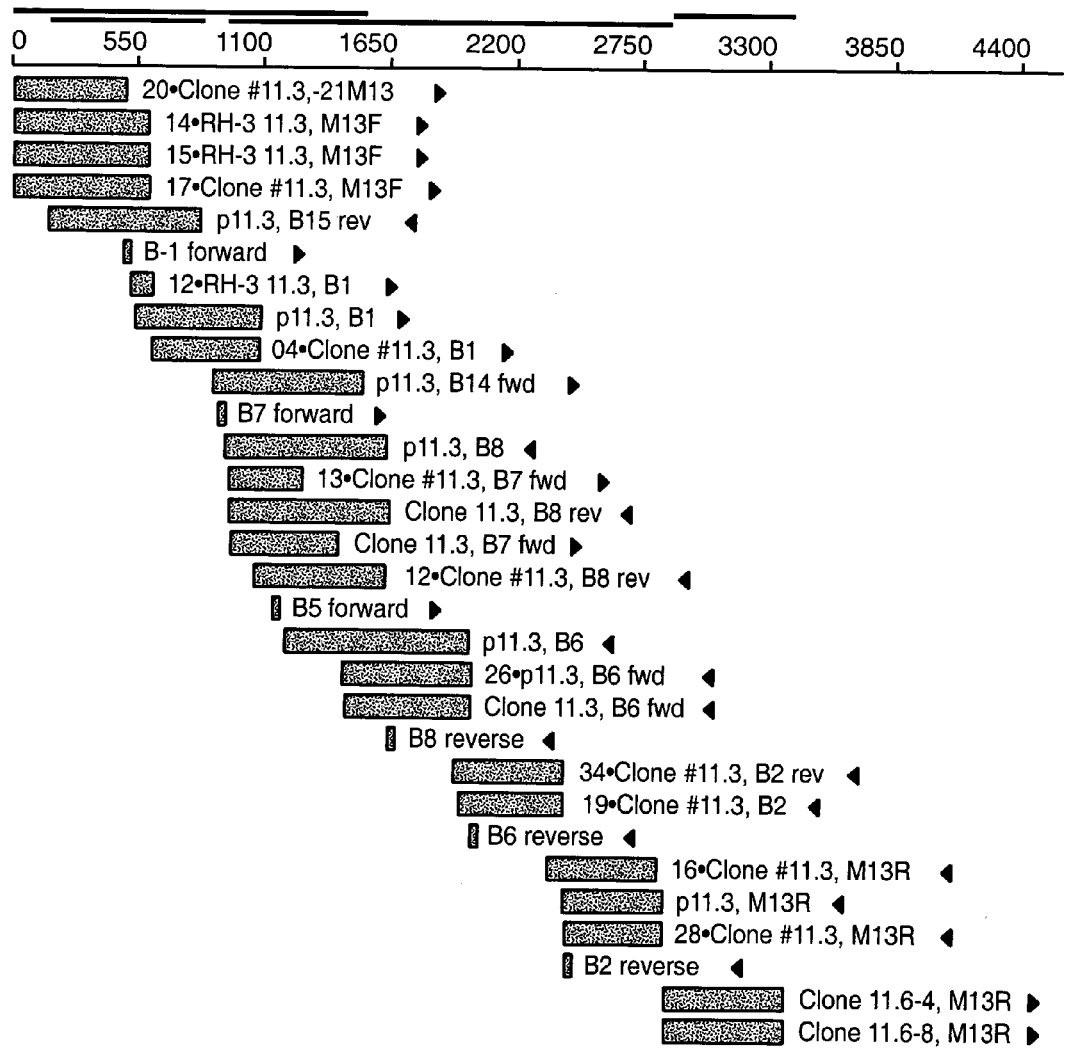
FIG._9

Primer Design for PCR Amplification of the SBAmyB Promoter.

The Pst11 primer was designed to add a PstI site on the 5' end of the SBAmyB promoter region. Base substitutions at the ATG codon created an NcoI site in the Nco11 primer (minus strand primer).

```
            GCCGAGGNCTAAAAGTGAATTAGG

PstI
5'-aactgcagaGCCGAGGNCTAAAAGTGAATTAGG-3'
              Pst11 primer
```

FIG._10A

Primer Design for PCR Amplification of the SBAmyB Promoter.

The Pst11 primer was designed to add a PstI site on the 5' end of the SBAmyB promoter region. Base substitutions at the ATG codon created an NcoI site in the Nco11 primer (minus strand primer).

```
                                   met codon
CATTGTAAAGACTTTGAGATTGGAGAGAAGATGAAGAGCT NcoI
        GACTTTGAGATTGGAGAGAccATGgAGAGCT NcoI
5'-AGCTCTCCATGGTCTCTCCAATCTCAAAGTC-3'
              Nco11 primer (inverse complement)
```

FIG._10B

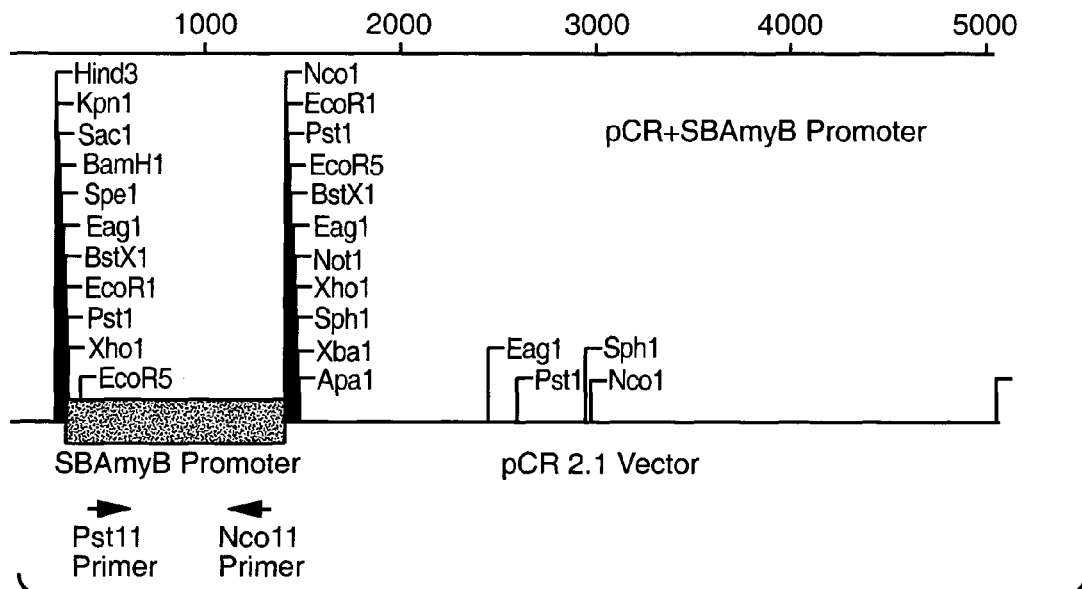
FIG._10C
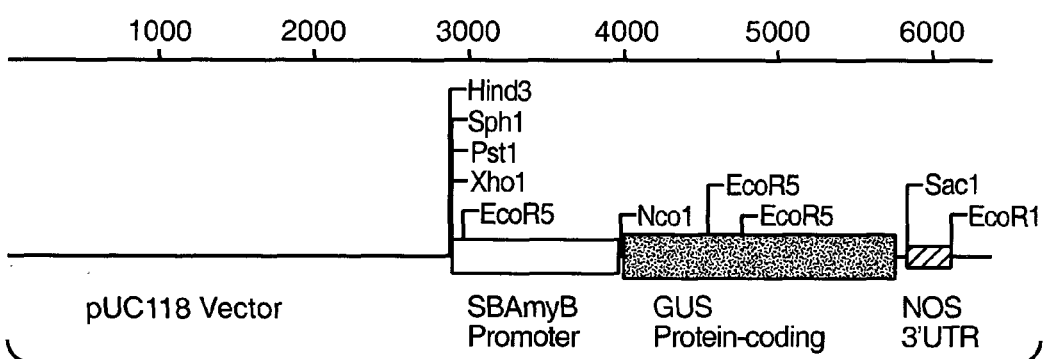
FIG._11A
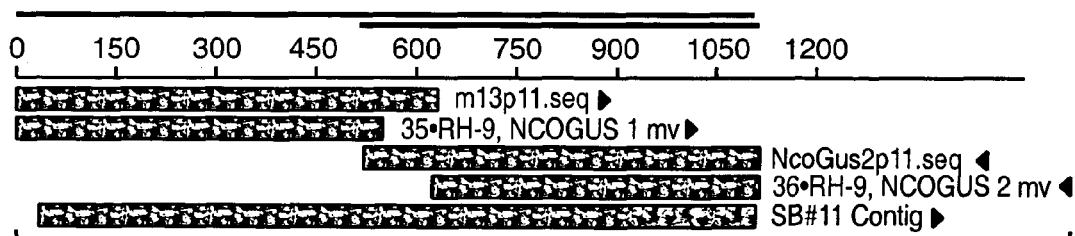
FIG._11B

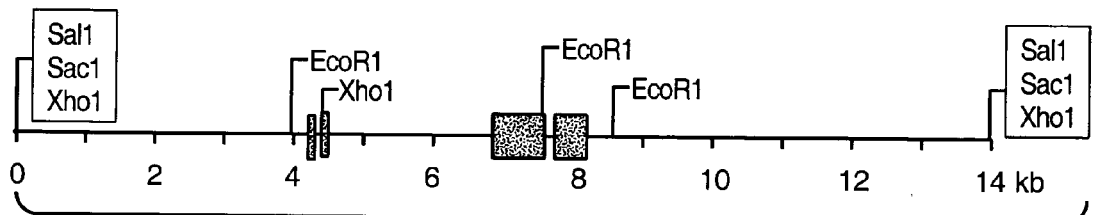
FIG._12A
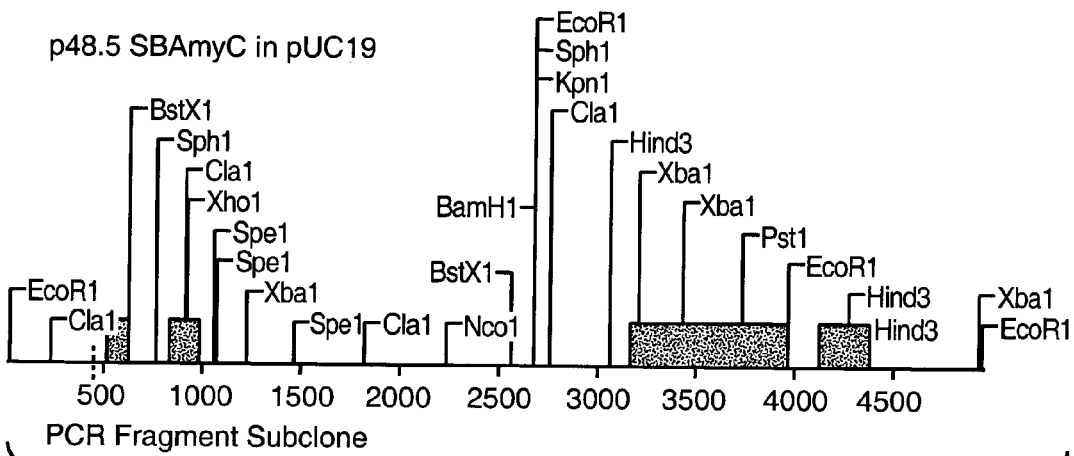
FIG._12B
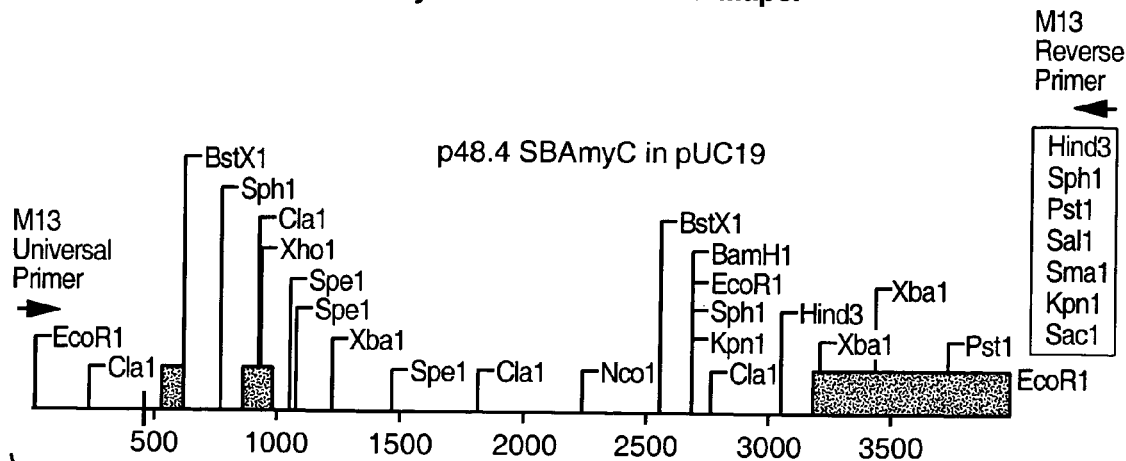
FIG._12C

FIG._12D

Primer Design for PCR Amplification of the SBAmyC Promoter.

The Pst48 primer was designed to add a PstI site on the 5' end of a vector sequence adjacent to the SBAmyC promoter region. Base substitutions at the ATG codon created an NcoI site in the Nco48 primer (minus strand primer). The GAGCTG sequence was added at the 5' end of the primer to increase the GC% and the annealing temperature.

```
                   pUC19 vector sequences
      PstI site                              EcoRI site
    AACTGCAGAACGTTGTAAAACGACGGCCAGTGAATTC Pst48 primer sequence
5'-AACTGCAGAACGTTGTAAAACGACGGCCAGTG-3'
```

FIG._13A

Primer Design for PCR Amplification of the SBAmyC Promoter.

The Pst48 primer was designed to add a PstI site on the 5' end of a vector sequence adjacent to the SBAmyC promoter region. Base substitutions at the ATG codon created an NcoI site in the Nco48 primer (minus strand primer). The GAGCTG sequence was added at the 5' end of the primer to increase the GC% and the annealing temperature.

```
                                  met codon
           GCTTCAAAAGTGGAGTGAACATGA primer binding site         NcoI site
     GCTTCAAAAGTGGAGTCAcCATGg Nco48 primer sequence
5'-GAGCTGCCATGGTCACTCCACTTTTGAAGC-3'
```

FIG._13B

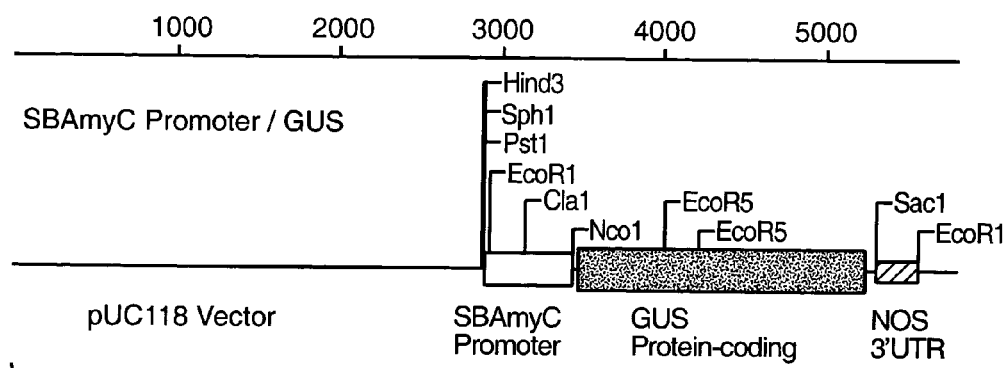
FIG._14A
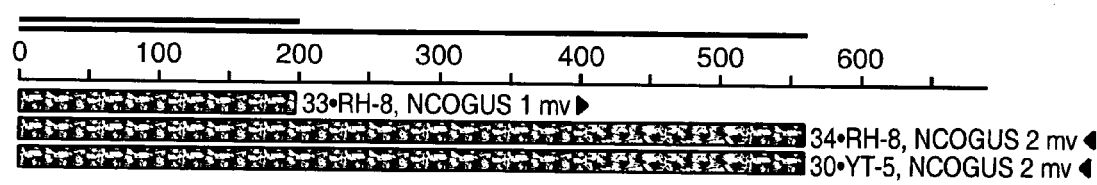
FIG._14B

Promoter Sequence Analysis via Pustell Matrix
Each mark on the grid represents a region of similarity between the two genes compared.
Window size = 10. Min. % score = 65%. Strand = both.

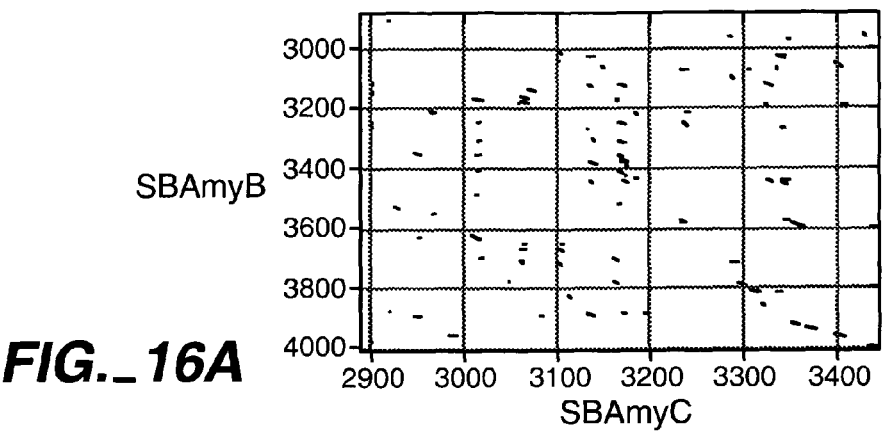

FIG._16A

Promoter Sequence Analysis via Pustell Matrix
Each mark on the grid represents a region of similarity between the two genes compared.
Window size = 10. Min. % score = 65%. Strand = both.

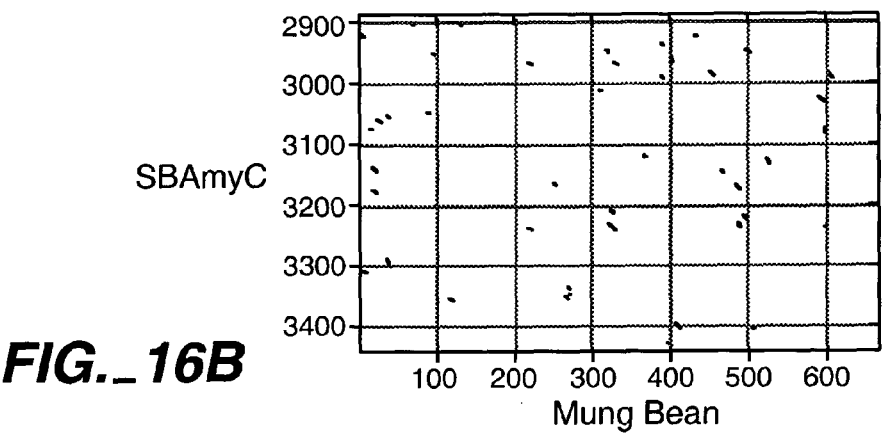

FIG._16B

Promoter Sequence Analysis via Pustell Matrix
Each mark on the grid represents a region of similarity between the two genes compared.
Window size = 10. Min. % score = 65%. Strand = both.

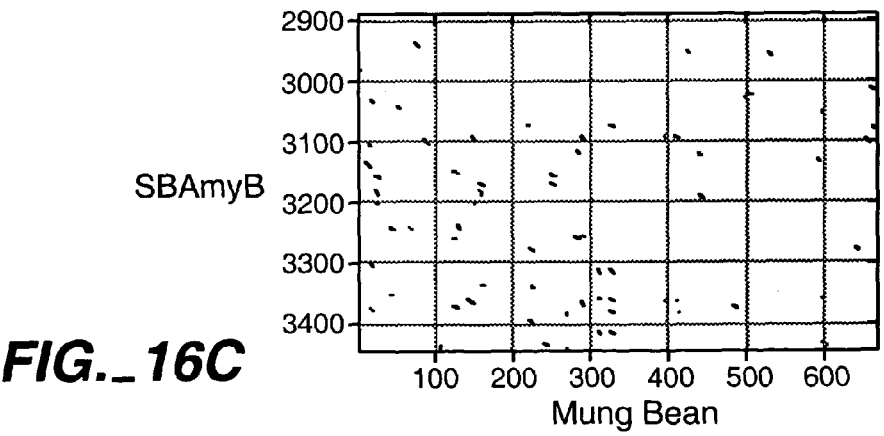

FIG._16C

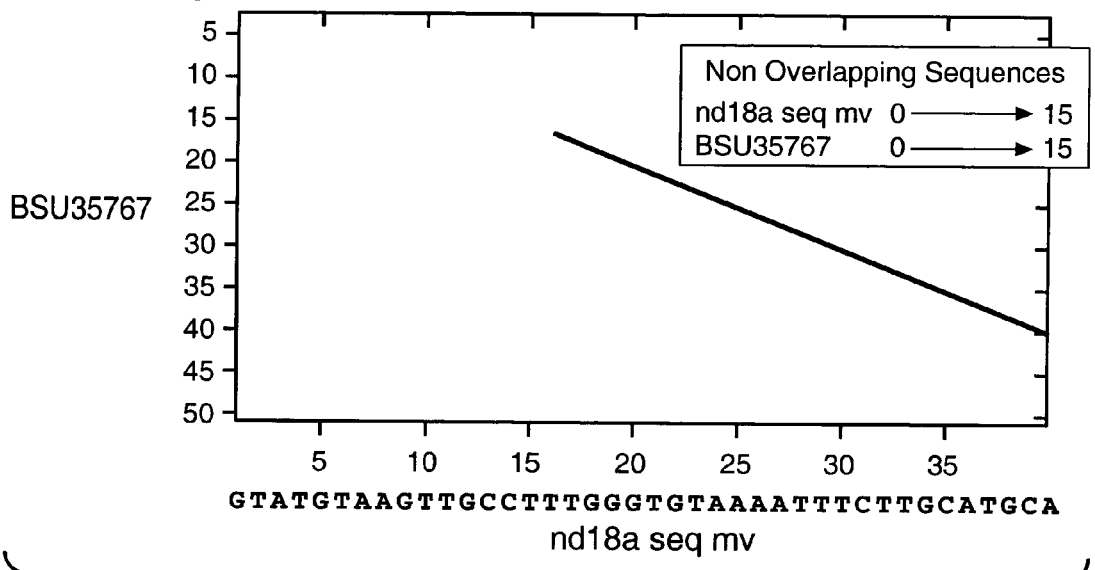
FIG._17
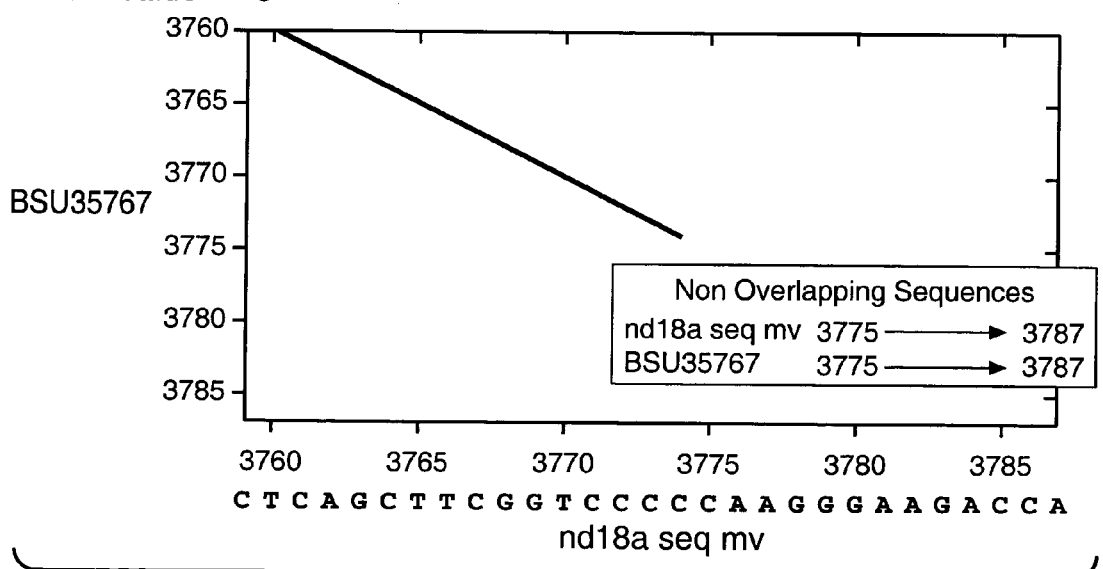
FIG._18

DNA SEQUENCES CAPABLE OF EXPRESSING FOREIGN PROTEINS AND METABOLITES IN DICOTYLEDONOUS PLANTS AND CELL CULTURE

BACKGROUND

1. Field of the Invention

This invention relates to specific DNA sequences which are capable of expressing foreign proteins and their metabolites in dicotyledonous plants and cell culture. Specifically, the present invention concerns the incorporation into a vector and expressing of the SBAmyB or SBAmyC gene of the sugar beet and recovering the product of the expressed gene.

2. Description of Related Art

The incorporation of the sugar beet genes SBAmyB or SBAmyC for α-amylase into other plants and seeds (particularly dicots) for expression has not been previously reported in the prior art.

The synthesis of α-amylase and levels of their mRNA are greatly induced under sucrose starvation. An increase of α-amylase synthesis is assumed to accelerate hydrolysis of cellular starch as an energy source when exogenous carbon source is depleted. Under normal growth condition with an adequate supply of sugars in the medium, the expression of α-amylase genes is subject to metabolite repression. It was observed that α-amylases synthesized by the cultured rice cells are secreted into the culture medium and can account for about 15–20% of the total proteins present in the medium during periods of sugar depletion.

It would therefore be advantageous to develop a gene expression system in plant cell culture by constructing a vector expressible in plant host cells utilizing the promoter and the signal peptide sequences of an α-amylase gene. Any foreign gene can be linked downstream of said promoter and signal peptide encoding sequences. This construct would then be used to transform a compatible plant host cell.

Theoretically, the α-amylase promoter would control the expression of foreign genes in said plant cells and the secretion of the proteins into the medium. Such an expression system therefore has a high potential to express and/or secrete large quantities of any important protein into the medium, greatly facilitating purification of the expressed protein.

To aid in the procedure of screening and/or to enhance further the expression efficiency of the gene expression system constructed above, said gene expression system may further comprise a suitable marker gene, a reporter gene, an antibiotic-resistance gene and/or an enhancer gene, all of which can be those well known by one of ordinary skill in the relevant art (see Maniatis, T., et al, "Molecular Cloning: A Laboratory Manual," pressed by Cold Spring Harbor Laboratory, $2^{nd}$ ed., 1989).

Some references of interest in this field include the following:

M. T. Chan et al. in *The Journal of Biological Chemistry*, vol. 269 (#26), pp. 17635–17641 discloses a novel gene expression system for plant cells based on the induction of α-amylase promoter by carbohydrate starvation. Specifically the 5'-regulatory region and putative signal sequence of a rice α-amylase gene. α-BSAmyA was fused into bacterial gene and introduced into rice, tobacco and potato systems.

R. L. Rodriguez, U.S. Pat. No. 5,888,789 discloses a process for protein production in plants.

R. L. Rodriguez in U.S. Pat. No. 6,048,973 discloses sugar-regulatory sequences in alpha amylase genes.

S.-M. Yu et al. in U.S. Pat. No. 5,460,952 describe gene expression comprising the promoter region of the alpha-amylase alpha-anylase genes. Specifically, a method is described for expression of Amy1 6, Amy1 7, Amy1 8 and Amy1 10 genes from rice.

B. Li et al., (1992) *Plant Physiology*, vol. 98, pp. 1277–1284 disclose research concerning the characterization and subcellular localization of debranching enzyme and endoamylase from the leaves of sugar beet.

B. R. Thomas et al, (1994) *Plant Physiol.*, vol. 106, pp. 1235–1239 teach metabolite signals which regulate gene expression and source/sink relations in cereal seedlings. During the seedling elongation stage, the Amy1A gene is expressed at a high level in the rice aleurone. The Amy3B, Amy3C and Amy3E genes are expressed at moderate levels. There is little or no expression of Amy 1B, Amy 1C, Amy 2A, or Amy 3A in the developing rice seedling.

D. Yamanouchi et al (1990), *Nucleic Acids Res.*, vol. 18 (#14), 4250, disclose the nucleic acid sequence of cDNA for α-amylase from cotyledon of germinating *vigna mungo* seeds.

D. M. Lawrence et al (1990) *Physiologia Plantarium*, vol. 78, pp. 421–429 disclose the mobilization of storage reserves during germination and early seedling growth of the sugar beet.

J. W. Kim et al (1997) *J. Plant Res.*, vol. 110, pp. 357–361 disclose the expression of α-amylase in cultured callus of French bean.

H. Takeuchi et al (1993) *Plant Physiol.* (*Plant Gene Register*), vol. 103, p. 1459 disclose the nucleotide sequence of the α-amylase gene from *vigna mungo*.

All patents, patent applications, articles, reference standards cited herein are incorporated by reference in their entirety.

The problem remains to successfully incorporate the genes of the sugar beet into other plants and seeds (particularly dicots) for expression to produce improved growth and biological properties. The present invention provides a novel method.

SUMMARY OF THE INVENTION

The present invention concerns a method for producing a gene product by expressing a gene encoding said gene product in angiosperm host cells, which method comprises:

a) constructing a vector expressible in angiosperm host cells, said vector comprising a promoter region derived from an amylase gene selected from SBAmyB or SBAmyC genes of the sugar beet and a gene encoding a desired gene product;

b) transforming a compatible angiosperm host cell with said vector;

c) cultivating the resulting transformant host cell to a sugar-depleted or sugar-free condition to promote the expression of said gene under the control of such promoter region; and d) recovering the product of the expressed gene.

In another aspect of the present invention, a method is provided for producing a gene product by expressing a gene encoding said gene product in plant host cells, comprising the steps of constructing a vector expressible in plant host cells, said vector comprising a promoter region derived from an α-amylase gene of a plant, and a gene encoding a desired gene product, said promoter region including the promoter and a DNA sequence encoding the signal peptide; transforming a compatible plant host cell with said vector;

cultivating the resultant transformant host cell in a suitable culture medium; and directly recovering the expressed gene product from said medium.

The sugar beet α-amylases are encoded by a multigene family which contains several distinct members. To understand how GA$_3$ and sugars regulate α-amylase gene expression in sugar beet, it is important to identify α-amylase cDNA clones representing different α-amylase genes. These clones, in turn, would be used to isolate their corresponding genomic clones.

In this invention, four of the α-amylase cDNA clones showing different restriction patterns were chosen for subcloning into the plasmid vector. The resultant clones were designated as SBAmyA, SBAmyB, SBAmyC, SBAmyD. The 3'-end regions of these cDNA clones were further subcloned and sequenced.

The expression pattern of these four α-amylase genes in cultured suspension cells of rice was determined with the use of the constructed gene-specific probes. Expression of α-SBAmyA and α-SBAmyB was induced by sugar depletion 6- and 37-fold, respectively, at day 12 and continued to increase at day 14. The results show that expression of the four α-amylase genes in response to carbohydrate starvation in the cultured cells is temporally and quantitatively regulated.

Consequently, an expression vector containing the promoter region of the α-amylase gene (αAmy A) was constructed in order to express β-glucuronidase (GUS) in transformed sugar beet cells. A hygromycin resistance gene hph placed downstream of the RNA promoter is used as a selectable marker.

Different transformation methods, such as electroporation of protoplasts or intact cells, particle bombardment, microinjection method, ultrasonic method, polyethylene glycol-mediated protoplast transformation, poly-L ornithine method, calcium phosphate method (Hain, R. et al (1985), Mol. Gen. Genet., 199: 161–168), and *Agrobacterium*-mediated transformation system are used to deliver the plasmid DNA into sugar beet. GUS expression was detected in either bombarded or electroporated cells two days after transfection. The results indicate that the α-amylase promoter-GUS chimeric genes are functional in sugar beet cells.

A reporter gene driven by an α-amylase promoter is further transferred and expressed in a sugar beet using a gene transfer system. The system comprises a plasmid containing chimeric genes of β-glucuronidase (GUS) and neomycin phosphotransferase (NPTII).

All new DNA sequences and the protein products thereof described herein are part of the present invention.

Features and advantages of the present invention will become apparent in the following detailed description with references to the accompanying drawings.

BRIEF DESCRIPTION OF THE FIGURES

FIG. 1 is a graphic representaion of the gamma component of viruses nd 18g seg and BSU 13917. (SEQ ID NO:5)

FIG. 2 is a graphic representation of the gamma component of BSU35767. (SEQ ID NO:6).

FIG. 3 is a schematic representation of the scale for restriction enzyme analysis of BSU 13917. (SEQ ID NO:5)

FIG. 4 is a schematic representation of the restriction enzyme analysis of BSU 35767 (SEQ ID NO:6) is equivalent to the BSMV alpha segment.

FIG. 5A is a schematic of the scale for the restriction enzyme analysis of BSU 35767. (SEQ ID NO:6)

FIG. 5B is a graphic representation of the restriction enzyme analysis for BSU 35767. (SEQ ID NO:7)

FIG. 6A is a schematic representation of BSMV T7 promoter construct of g+gbrs+vector as T7-g-gfp showing the RNA transcript region and polypeptide coding region.

FIG. 6B is a schematic representation of BSMV T7 promoter construct of a+vector as T7-a showing the RNA transcript region and the polypeptide coding region.

FIGS. 7A, 7B and 7C concern sugar beet α-amylase gene phylogeny, expression and genomic clone isolation, respectively.

FIGS. 8A and 8B are graphic representations of SBAmyB gene restriction maps, FIG. 8A is λSB #11 in EMBL sp6/T7, and FIG. 8B is 2.8 kb Sac 1 fragment from FIG. 8A.

FIG. 9 is a schematic representation of SBAmyB gene—DNA sequencing strategy.

FIGS. 10A (SEQ ID NOS 12 & 13) and 10B (SEQ ID NOS 14–16) are representations of primer design for PCR amplification of SBAmyB promoter. FIG. 10C is a representation of SBAmyB promoter fragment subclone.

FIG. 11A is a schematic representation of SBAmyB promoter/GUS—restriction map. FIG. 11B is the SBAmyB/Gus—DNA sequencing strategy.

FIG. 12A is a schematic representation of SBAmyC in EMBL 3SP6/T7. FIG. 12B is a schematic representation of p48.5 SBAmyC in PUC19. FIG. 12C is p48.4 SBAmyC in pUC19. FIG. 12D is a schematic representation of SBAmyC gene—DNA sequencing strategy.

FIG. 13A (SEQ ID NOS 17 & 18) and 13B (SEQ ID NO: 19–21) are representations of primer design for PCR amplification for SBAmyC promoter. FIG. 13C is a restriction map for SBAnyC promoter fragment subclone.

FIG. 14A is a schematic representation of the SBAmyC promoter/GUS restriction map. FIG. 14B is a schematic representation of the SBAmyC promoter/GUS—DNA sequencing strategy.

FIGS. 16A, 16B and 16C are a graphic representation of the sequence analysis of the SBAmyB and SBAmyC genes using a Pustell matrix.

FIG. 17 is a graphic representation of the alpha component of virus (SEQ ID NO: 22): nd18a mv and BSU 35767 (SEQ ID NO: 6).

FIG. 18 is a graphic representation of the alpha component for BSU 35767 (SEQ ID NO: 6).

DETAILED DESCRIPTION OF THE INVENTION AND PREFERRED EMBODIMENT

Figure 15:
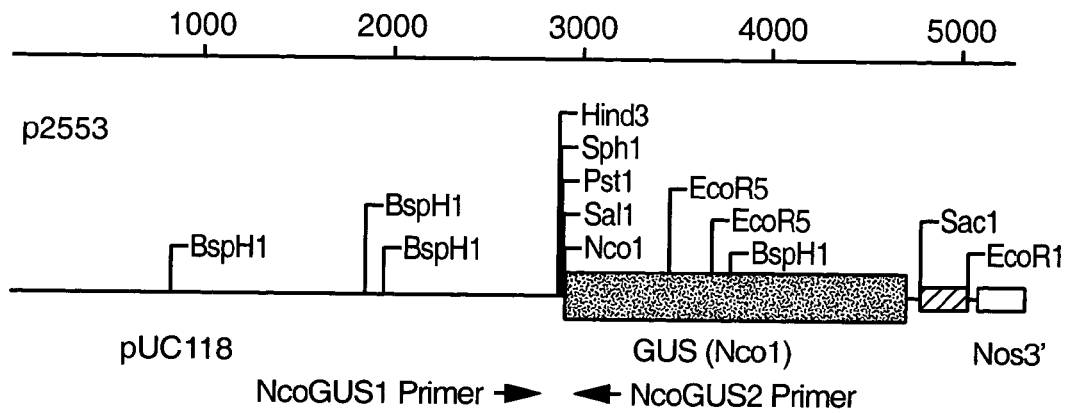
FIG. 15 is a schematic representation of p2553 Nco-Gus vector.

Sugar beet (Beta vulgaris) α-amylase genes, SBAmyA and SBAmyB and their promoters have been isolated and characterized from a sugar beet genomic DNA library. These genes are expressed in a regulated and tissue-specific fashion in the germinating sugar-beet seed, and in sugar beet cell culture. By fusing the promoters from these genes to foreign genes of commercial interest, it is possible to: (1) enhance agronomic traits like seedling vigor or disease resistance, (2) after carbohydrate biosynthesis in the developing or germinating dicot seed and (3) express commercially important foreign proteins in transgenic cells and tissues of dicot plants, including germinating seeds and tissue culture cells.

The SBAmyB and SBAmyC are sugar beet α-amylase genes expressed during seed germination and early seedling-development as well as in sugar beet cell suspension cultures. SBAmyB and SBAmyC are two members of a gene family consisting of four genes. The highest level of expression of SBAmyB and SBAmyC is from 2 to 3 days after imbibition of the seeds. The α-amylase encoded by these genes helps to degrade starch into the sugars needed to support seedling development.

Two isozymes of α-amylase identified in sugar beet seedlings may represent the gene products of the SBAmyB and SBAmyC genes. These two isozymes are distinguishable by their pH optima (4.5 vs. 6.5).

The 5'-flanking regions preceding the translation initiation sites in these genes are expected to contain the regulatory DNA sequences that control the initiation of gene transcription. Typically these cis-element sequences, or promoters, are found within 500–1000 bases from the translation start site.

Chimeric genes containing the sugar beet α-amylase promoter and the protein-coding region of a commercially important foreign gene can be constructed and introduced by transformation and stable integration into the genome of sugar beet (or other dicotyledonous) plants in a way that permits the long term, regulated and tissue specific expression of the foreign protein. Foreign genes expressed in this way may produce improved plant cultivars for use in agriculture. Because these promoters also function in sugar beet cell cultures, these same chimeric genes can be expressed in plant cell bioreactors, similar to the microbial and mammalian cell fermentation systems. These promoters may provide a basis for using transgenic dicot plants (or dicot cell cultures) as an efficient, low-cost, expression system for commercially important proteins.

Because these promoters are regulated and tissue specific, they may be useful in elevating or reducing these levels of key enzymes in a plant metabolic pathway. This approach is called "metabolic engineering" and it has been used successfully to produce useful metabolites in microbes, plants and animal systems. There are a number of plant metabolites that could enhance the nutritional and health benefits of various foods, if expressed in the right concentration and in the right tissue of the plant. Compounds like sulforaphanes in broccoli, lycopenes in tomato and beta-carotene in carrots have well known antioxidant and anticancer properties and may also reduce the level of heart disease when consumed in the appropriate levels.

The sugar beet α-amylase promoters described herein are fused to genes encoding enzymes in the pathway of interest so as to increase or decrease their expression (antisense gene constructs are typically used to reduce or eliminate the expression of genes in plants).

1. Promoter sequences that direct the expression of the SBAmyB and SBAmyC genes are found within the 500–1000 bases of 5' flanking region of the genes.

2. With these sequences, it will be possible to achieve the regulated expression and secretion of foreign proteins in seedlings and tissue cultures of sugar beet and other dicot plants by: (1) fusing the protein-coding region of foreign genes to any promoter containing cis-elements identical or similar sequences to those found in the SBAmyB or SBAmyC promoter, (2) fusing foreign genes to combinations of one or more of these sequences and (3) fusing foreign genes to new seedling-expressed promoters created by inserting one or more of these SBAmyB or SBAmyC promoter sequences into a plant promoter that is not normally seedling-expressed.

Also, sugar beet produces a starchy seed, with reserve materials stored in the perisperm tissue (as described in Elamrani in 1992). Senescence of the perisperm in seeds from this dicot plant may be functionally similar to endosperm breakdown in the cereal seed endosperm. The cereal alpha-amylases (E.C. 3.2.1.1) of glycosyl hydrolase family 13 (as described by Henrissat in 1991) are among the most extensively studied plant genes, but alpha-amylases of dicot plants have received much less attention. Cereals have moderate sized gene families of alpha-amylase, with ten alpha-amylase genes per haploid genome in rice. These rice alpha-amylases are classified into three subfamilies, with subfamilies 1 and 2 regulated by phytohormones GA and ABA and subfamily 3 induced in response to sugar starvation (as described by Thomas in 1994). Thus, it is of interest to determine whether similar classes of alpha-amylases exist within the dicot species.

Alpha-amylase genes of cereals typically have a high (GC) content, while dicot genes typically are closer to 50% GC. Thus, cereal alpha-amylase genes are unlikely to be successful as probes for isolation of alpha-amylase genes from dicot plants. Conserved regions of sequence in the cereal alpha-amylase gene family were targetted for isolation via a PCR approach. Degenerate oligonucleotide primers were made in these conserved regions based on the alpha-amylase sequence from mung bean. This enabled alpha-amylase gene fragments to be amplified from genomic DNA of sugar beet. These PCR products were cloned into plasmids, classified by restriction analysis and submitted for automated DNA sequencing. These fragments span 456 bases within exon 2. Analysis of sequence relationships among these partial gene sequences suggest two subgroups of the sugar beet alpha-amylases, with >90% similarity in the SBAmyB and SBAmyC group and within the SBAmyA and SBAmyD group. The sugar beet amylases are 75–79% similar to the mung bean amylase and 63–68% similar to the rice amylase (as described by Huang in 1990a; and Huang in 1990b) genes tested. Thus, this region of the sequence does not allow the sugar beet alpha-amylases to be associated with amylase subgroups of other plant species.

Table 1A below describes the pair wise similarity of alpha-amylase from sugar beet and other dicot plants.

TABLE 1A

Pairwise similarity of alpha-amylases from sugar beet and other dicot plants.

|  | SBAmyA | SBAmyB | SBAmyC | SBAmyD | amyVm1 | Amy1A | Amy3D | GenBank # |
|---|---|---|---|---|---|---|---|---|
| SBAmyA | — | | | | | | | |
| SBAmyB | 79% | — | | | | | | |
| SBAmyC | 81% | 94% | | | | | | |
| SBAmyD | 99% | 79% | 81% | — | | | | |
| amyVm1 | 75% | 77% | 79% | 75% | — | | | X73301 |
| Amy1A | 64% | 65% | 65% | 63% | 67% | | | X16509 |
| Amy3D | 64% | 64% | 63% | 68% | 67% | 83% | — | X16509 |

Table 1 which follows shows the DNA sequence for SBAmyA having 460 base pairs (SEQ ID NO: 1).

Table 2 which follows is the DNA sequence for SBAmyB having 460 base pairs (SEQ ID NO: 2).

Table 3 which follows is the DNA sequence for SBAmyC having 460 base pairs (SEQ ID NO: 3).

Table 4 which follows is the DNA sequence for SBAmyD having 457 base pairs (SEQ ID NO: 4).

TABLE 1

SBAmyA

| | |
|---|---|
| LOCUS | SBAMYA 460 BP DS-DNA |
| DEFINITION | B. vulgaris alpha-amylase SBAmyA gene, partial cds |
| ACCESSION | — |
| KEYWORDS | — |
| SOURCE | PCR amplification from beet genomic DNA |
| ORGANISM | Beta vulgaris |
| | Eukaryota; Viridiplantae; Streptophyta; Embryophyta; Tracheophyta; euphyllophytes; Spermatophyta; Magnoliophyta; eudioctyledons; core eudicots; Caryophyllidae; Caryophyllales; Chenopodiaceae; Beta |
| REFERENCE | |
| AUTHORS | B R Thomas, E Bowman, R L Rodriguez |
| TITLE | Four alpha-amylase genes in sugar beet (*Beta vulgaris* L.) |
| JOURNAL | Plant Gene Reporter (2000) submitted |
| FEATURES | From   To/Span   Description |
| source | 1   460   exon 2 (partial) |
| BASE COUNT | 146 A   79 C   99 G   133 T   3 OTHER |
| ORIGIN | |

```
  1 AAATCCTAGA  GTACAAAAAG  AGTTAATAGA  TTGGATGAAT  TGGCTTAAAA  CAAGTATAGG
 61 CTTTGATGGT  TGGAGATTAG  ATTTCGTTAA  AGGATATTCT  CCTAGCATAA  CTAAATTATA
121 TATGGATCAA  ACTAAGCCAG  ATTTCGCCGG  TTGGAGAGCT  ATGGGACTCC  ATTACTTATC
181 TTAATGGTGC  ACCCCGATTA  CAACCAAGAC  GGACATCGAN  ACGAGCTAGC  TAGATGGGGT
241 TCAAGCCTCT  GGTGGAGGAG  TTGTTACTGC  CTTTGATTTT  ACTACAAAAG  GNATTCTTCA
301 ATATGCAGTG  CAAGGACAAT  GGTGGAGAAT  GAGAGACCCT  AATGGTAGAC  CTAGTGGACT
361 TATTGGAATT  TTACCAAAAA  ATGCTGTTAC  TTTCCTTGAT  AACCATGATA  CTGGATCTAG
421 TCAAAAACTT  TGNCCTTTTC  CACCTGATAA  AGTCATGCAA
```

TABLE 2

ABAmyB

| | |
|---|---|
| LOCUS | SBAMYB 460 BP DS-DNA |
| DEFINITION | B. vulgaris alpha-amylase SBAmyB gene, partial cds |
| ACCESSION | — |
| KEYWORDS | — |
| SOURCE | PCR amplification from beet genomic DNA |
| ORGANISM | Beta vulgaris |
| | Eukaryota; Viridiplantae; Streptophyta; Embryophyta; Tracheophyta; euphyllophytes; Spermatophyta; Magnoliophyta; eudioctyledons; core eudicots; Caryophyllidae; Caryophyllales; Chenopodiaceae; Beta |
| REFERENCE | |
| AUTHORS | B R Thomas, E Bowman, R L Rodriguez |
| TITLE | Four alpha-amylase genes in sugar beet (*Beta vulgaris* L.) |
| JOURNAL | Plant Gene Reporter (2000) submitted |
| FEATURES | From   To/Span   Description |
| source | 1   457   exon 2 (partial) |
| BASE COUNT | 149 A   76 C   98 G   133 T   1 OTHER |
| ORIGIN | |

```
  1 AAATCCAAGG  GTACAAAGAG  AACTAGTTGA  TTGGATGAAT  TGGCTGAAGA  CGGAAATGG
 61 TTTTGACGGG  TGGAGATTTG  ATTTGTCAA  GGGATATGCT  CCCAGCATTA  CTAAAATTTA
121 CATGGAAGAG  ACTAGGCCAG  ATTTTGCAGT  TGGAGAGCTT  TGGGATTCCA  TTAATTATGA
181 TCCAGACGGT  AAGCCAGACT  ACAATCAAGA  CGGACCTCGA  AATGAACTAG  CTGGATGGGT
241 ACAAGCTGCA  GGTGGTGGTG  TTATTGCTGC  ATTTGATTTC  ACCACCAAAG  GTGTTCTTCA
301 AGCTGCCGTG  CAAGGAGAGT  GGTGGAGAAT  GAAAGATTCT  AGTGGTAGGC  CTAGTGGGTT
361 AATAGGAATT  ATGCCTAAAA  ATGCTGTCAC  TTTTATTGAT  AATCATGACA  GTGGTTCCAC
421 ACAAAGGTTA  TGGCCTTTTC  CTGCAGACAA  AGTAATGCAA
```

TABLE 3

SBAmyC

| | |
|---|---|
| LOCUS | SBAMYC 460 BP DS-DNA |
| DEFINITION | B. vulgaris alpha-amylase SBAmyC gene, partial cds |
| ACCESSION | — |
| KEYWORDS | — |

TABLE 3-continued

SBAmyC

| SOURCE | PCR amplification from beet genomic DNA | | | | | |
|---|---|---|---|---|---|---|
| ORGANISM | *Beta vulgaris* | | | | | |
| | Eukaryota; Viridiplantae; Streptophyta; Embryophyta; Tracheophyta; | | | | | |
| | euphyllophytes; Spermatophyta; Magnoliophyta; eudioctyledons; core | | | | | |
| | eudicots; Caryophyllidae; Caryophyllales; Chenopodiaceae; Beta | | | | | |
| REFERENCE | | | | | | |
| AUTHORS | B R Thomas, E Bowman, R L Rodriguez | | | | | |
| TITLE | Four alpha-amylase genes in sugar beet (*Beta vulgaris* L.) | | | | | |
| JOURNAL | Plant Gene Reporter (2000) submitted | | | | | |
| FEATURES | From | To/Span | Description | | | |
| source | 1 | 460 | exon 2 (partial) | | | |
| BASE COUNT | 139 A | 75 C | 115 G | 131 T | 0 OTHER | |
| ORIGIN | | | | | | |
| 1 | TAATCCAAGA | GTACAAAAGG | AGTTAGTCGA | TTGGATGAAT | TGGCTCAAGA | CAGAAATTGG |
| 61 | TTTTGACGGA | TGGAGATTTG | ATTTTGTTAA | GGGATATGCT | CCTAGCATTA | CCAAAATTTA |
| 121 | CATGGAAAAA | ACTAGGCCTG | ATTTTGCAGT | TGGAGAGCTT | TGGGATTCCA | TTACATATGA |
| 181 | CCCGGATGGT | AAGCCAGACT | ATAACCAAGA | CGGACCTCGA | AATGAACTAG | CTGGATGGGT |
| 241 | ACAAGCTGCA | GGTGGTGGTG | TTATTGCTGC | ATTTGATTTC | ACTACCAAAG | GTGTTCTTCA |
| 301 | AGCTGCTGTT | CAAGGAGAAT | GGTGGAGAAT | GAAAGATTCT | AATGGTAGGC | CTAGTGGGTT |
| 361 | GATAGGAATT | ATGCCTAAAA | ATGCTGTCAC | TTTTATTGAT | AATCATGACA | CTGGTTCCAC |
| 421 | ACAAAGGTTA | TGGCCTTTTC | CCGCAGACAA | AGTCATGCAA | | |

TABLE 4

SBAmyD

| LOCUS | SBAMYD 457 BP DS-DNA | | | | | |
|---|---|---|---|---|---|---|
| DEFINITION | *B. vulgaris* alpha-amylase SBAmyD gene, partial cds | | | | | |
| ACCESSION | — | | | | | |
| KEYWORDS | — | | | | | |
| SOURCE | PCR amplification from beet genomic DNA | | | | | |
| ORGANISM | *Beta vulgaris* | | | | | |
| | Eukaryota; Viridiplantae; Streptophyta; Embryophyta; Tracheophyta; | | | | | |
| | euphyllophytes; Spermatophyta; Magnoliophyta; eudioctyledons; core | | | | | |
| | eudicots; Caryophyllidae; Caryophyllales; Chenopodiaceae; Beta | | | | | |
| REFERENCE | | | | | | |
| AUTHORS | B R Thomas, E Bowman, R L Rodriguez | | | | | |
| TITLE | Four alpha-amylase genes in sugar beet (*Beta vulgaris* L.) | | | | | |
| JOURNAL | Plant Gene Reporter (2000) submitted | | | | | |
| FEATURES | From | To/Span | Description | | | |
| source | 1 | 457 | exon 2 (partial) | | | |
| BASE COUNT | 149 A | 76 C | 98 G | 133 T | 1 OTHER | |
| ORIGIN | | | | | | |
| 1 | AAATCCTAGA | GTACAAAAAG | AGTTAATAGA | TTGGATGAAT | TGGCTTAAAA | CAAGTNTAGG |
| 61 | CTTTGATGGT | TGGAGATTAG | ATTTCGTTAA | AGGATATTCT | CCTAGCATAA | CTAAATTATA |
| 121 | TATGGATCAA | ACTAAGCCAG | ATTTCGCGGT | TGGAGAGCTA | TGGGACTCCA | TTACTTATCT |
| 181 | TAATGGTGCA | CCTGATTACA | ACCAAGACGG | ACATCGAAAC | GAGCTAGCTA | GATGGGTTCA |
| 241 | AGCCTCTGGT | GGAGGAGTTG | TTTACTGCCTT | TGATTTTACT | ACAAAAGGAA | TACTTCAATA |
| 301 | TGCAGTGCAA | GGACAATGGT | GGAGAATGAA | AGACCCTAAT | GGTAGACCTA | GTGGACTTAT |
| 361 | TGGAATTTTA | CCAAAAAATG | CTGTTACTTT | CCTTGATAAC | CATGATACTG | GATCTAGTCA |
| 421 | AAAACTTTGG | CCTTTTCCAC | CTGATAAAGT | CATGCAA | | |

The products herein are described in the figures:

FIG. 1 is a graphic representaion of the gamma component of viruses nd 18g seg and BSU 13917. (SEQ ID NO: 5)

FIG. 2 is a graphic representation of the gamma component of BSU35767. (SEQ ID NO: 6).

FIG. 3 is a schematic representation of the scale for restriction enzyme analysis of BSU 13917. (SEQ ID NO: 5)

FIG. 4 is a schematic representation of the restriction enzyme analysis of BSU 35767 (SEQ ID NO: 6) is equivalent to the BSMV alpha segment.

FIG. 5A is a schematic of the scale for the restriction enzyme analysis of BSU 35767. (SEQ ID NO: 6)

FIG. 5B is a graphic representation of the restriction enzyme analysis for BSU 35767. (SEQ ID NO: 7)

FIG. 6A is a schematic representation of BSMV T7 promoter construct of g+gbrs+vector as T7-g-gfp showing the RNA transcript region and polypeptide coding region.

FIG. 6B is a schematic representation of BSMV T7 promoter construct of a+vector as T7-a showing the RNA transcript region and the polypeptide coding region.

EXPERIMENTAL

The Examples described herein below are to further explain and describe the invention. They are not to be construed to be limiting in any way.

Reagents, compounds, solvents, media, cultures, vectors, promoters DNA sequences as described herein are used as received from the supplier unless otherwise noted.

Example 1

General Procedures and Protocols—Sugar Beet Genomic DNA Isolation

1. Grind 2.5 g of leaf tissue in liquid nitrogen thoroughly with mortar and pestle. After tissue is ground to a fine powder, immediately add 6–10 mL of pre-chilled DNA Extraction Buffer and continue grinding until a soupy broth is formed (note: if extract is too pasty, add 1–2 mL more of DNA Extraction Buffer and continue griding).

2. Use cut-off P-1000 pipet tip to aliquot approximately 1.5 mL into the two labeled microfuge tubes and place on rack in ice bath.

3. Repeat steps (1) and (2) for each sample until all samples have been ground.

4. Centrifuge samples at 10K for 5 min. to pellet cellular debris. Pour off supernatants and resuspend pellets in 300 μl each of DNA Extraction Buffer and Nuclei Lysis Buffer using a vortexer.

5. Add 120 μl of 5% (w/v) Sarkosyl, vortex to mix and heat for 30 min. at 65 degrees Celsius.

6. Add 600 μl of Chloroform:Isoamyl Alcohol (24:1) and vortex on 4½ setting until an emulsion is formed. Centrifuge samples at 14K for 5 min. to separate organic and aqueous layers.

7. Transfer aqueous top layer (avoiding cloudy interface) to new microfuge tubes containing 700 μl ice-cold Isopropanol. Invert tubes to mix until a stringy DNA precipitate is observed.

8. Centrifuge tubes at 14K for 5 min. to pellet precipitated DNA. Pour off supernatants and wash pellets in 700 μl 100% Ethanol. Centrifuge tubes at 14K for 5 min. and carefully pour off supernatants. Wash pellets with 400 μl 70% Ethanol, centrifuge at 14K for 1 min. and again carefully pour off supernatants (note: DNA pellets may be transparent and loose after 70% Ethanol wash).

9. Remove excess alcohol from pellets by carefully dabbing tubes on clean paper towels. Place samples in microfuge tube rack in vacuum dessicator and use vacuum pump to put a vacuum on dessicator. Leave samples in vacuum dessicator for at least 20 mm., then slowly release vacuum and check to see if DNA pellets are dry.

10. Resuspend DNA in 30 μl TE and store at −20° C.

Phase Separation

Store the homogenates for 5 minutes at room temperature to permit the complete dissociation of nucleoprotein complexes. Next, supplement the homogenate with 0.1 ml BCP or 0.2 ml chloroform per 1 ml of TRI REAGENT®, cover the samples tightly and shake vigorously for 15 seconds. Store the resulting mixture at room temperature for 2–15 minutes and centrifuge at 12000 g (max.) for 15 minutes at 4° C. Following centrifugation, the mixture separates into a lower red, phenol-chloroform phase, interphase, and the colorless upper aqueous phase. RNA remains exclusively in the aqueous phase whereas DNA and proteins are in the interphase and organic phase. The volume of the aqueous phase is about 60% of the volume of TRI REAGENT® used for the homogenziation.

BCP is less toxic than chloroform and its use for phase separation decreases possibility of contaminating RNA with DNA (3).

Chloroform used for phase separation should not contain isoamyl alcohol or any other additive.

RNA Precipitation

Transfer the aqueous phase to a fresh tube, and save the interphase and organic phase at 4 C for subsequent isolation of DNA and proteins. Precipitate RNA from the aqueous phase by mixing with isopropanol. Use 0.5 ml of isopropanol per 1 ml of TRI REAGENT® used for the initial homogenization. Store samples at room temperature for 5–10 min and centrifuge at 12 000 g (max.) for 8 minutes at 4–25 C. RNA precipitate (often invisible before centrifugation) forms a gel-like pellet on the side and bottom of the tube.

RNA Wash

Remove supernatant and wash the RNA pellet once with 75% ethanol by vortexing with subsequent centrifugation at 7 500 g (max.) for 5 minutes at 4–25° C. Add at least 1 ml of 75% ethanol per 1 ml of TRI REAGENT® used for the initial homogenization.

If the RNA pellet accumulates on a side of the tube and has tendency to float, perform the ethanol wash at 12 000 g.

RNA Solubilization

At the end of the procedure, briefly dry the RNA pellet by air-drying or under vacuum (5–10 min). It is important not to let the RNA pellet dry completely as this will greatly decrease its solubility. Do not dry RNA by centrifugation under vacuum. Drying is not necessary for solubilization of RNA in FORMAzol®. Dissolve RNA in FORMAzol® (stabilized formamide, cat. No. FO-121), water or 0.5% SDS by passing the solution a few times through a pipette tip, and incubating for 10–15 minutes at 55–60° C. Water or the SDS solution used for RNA solubilization should be made Rnase-free by diethyl pyrocarbonate (DEPC) treatment.

The REAGENT® isolates a whole spectrum of RNA molecules, rarely observed in RNA preparations isolated by other methods. The ethidium bromide straining of RNA separated in agarose gel (or methylene blue staining of a hybridization membrane after the RNA transfer) visualizes two predominant bands of small (~2 kb) and large (~5 kb) ribosomal RNA, low molecular weight (0.1–0.3 kb) RNA, and discrete bands of high molecular weight (7–15 kb) RNA.

The final preparation of total RNA is free of DNA and proteins and has a 260/280 ratio 1.6–1.9.

Expected yield: A) tissues (μg RNA/mg tisue): liver, spleen, 6–10 μg: kidney, 3–4 μg; skeletal muscles, brain, 1–1.5 μg; placenta, 1–4 μg; B) cultured cells (μg RNA/$10^6$ cells): epithelial cells. 8–15 μg; fibroblasts, 5–7 μg.

An additional isolation step may be required for samples with a high content of proteins, fat, polysaccharides or extracellular material such as muscles, fat tissue and tuberous parts of plants. Following homgenization, remove insoluble material from the homogenate by centrifugation at 12000 g for 10 minutes at 4° C. The resulting pellet contains extracellular membranes, polysaccharides and high molecular weight DNA, while the supernatant contains RNA. In samples from fat tissue, an excess of fat collects as a top layer which should be removed. Transfer the clear supernatant to a fresh tube and proceed with the phase separation and other steps of RNA isolation as described above. High molecular weight DNA can be recovered from the pellet by following steps 2 and 3 of the DNA isolation protocol.

Northern Blot of Sugar Beet (3 Day Post-inhibition and Mature Leaf)

RNA Isolation

Follow modified TRI-REAGENT protocol below:

(1) Place 0.5 g sugar beet leaf or seedling tissue in a 15 ml sterile Falcon tube and freeze by dipping tube in liquid nitrogen. Grind sample into a fine powder using a pre-frozen glass stirring rod.

(2) Add 7 ml of TRI-REAGENT (in fume hood) and homogenize using a hand-held homogenizer.

(3) Spin down cell debris in a centrifuge at 10,000×g for 10 min at 4 degrees Celsius.

(4) Transfer supernatant (using a sterile disposable glass pipet) into a new 15 ml Falcon tube, add 1.4 ml Chloroform (using a sterile disposable glass pipet) and shake sample vigorously for 15 sec. Store sample at room temperature for 2–15 min. and centifuge at 10,000×g fro 15 min. at 4 degrees Celsius.

(5) Transfer the aqueous phase to a new 5 ml Falcon tube (using a sterile disposable glass pipet) and add 1.75 ml of high-salt precipitation solution and 1.75 ml of isopropanol (using a sterile disposable glass pipet) and mix well by inversion. Store sample at room temperature for 5–10 mm., then centrifuge at 10,000×g for 8 min. at 4 degrees Celsius.

(6) Pour-off supernatant and resuspend pellet in 7 ml of 75% ethanol (using a sterile disposable glass pipet) and centrifuge at 7500×g for 5 min. at 4 degrees Celsius.

(7) Pour-off supernatant and allow pellet to air-dry (but not completely). Resuspend RNA pellet in FORMAzol solubilization solution (using a sterile filtered pipet tip) incubate sample at 50–55 degrees Celsius for 10–15 min. to resuspend RNA.

Spectrophotometric Quantitation (1) Dilute 3 μl FORMAzol in 0.5 ml of DEPC-treated ddH$_2$O in 1.5 ml microfuge tubes.

(2) Measure Absorbance at 325 nm, 280 nm, 260 nm and 230 nm to check purity and yield of RNA sample. Determine A260/A280 value (should be between 1.6 and 2.0)

Procedures:

A. 1. Standard Procedure

After the appropriate volumes of probe and sample RNA have been mixed together, the salt concentration is adjusted if necessary with NH$_4$OAc and 1. Mix predetermined volumes of sample RNA and labeled probe (see above) in a 1.5 ml microcentrifuge tube. A typical experiment might include 20 tubes with different amounts or sources of sample RNA.

2. For each different probe used, include two control tubes containing the same amount of labeled probe used for the experimental tubes in Step 1 with enough Soln. C (yeast RNA; 5 μg/μl) to be equivalent to the highest amount of sample RNA.

3. Adjust the concentration of NH$_4$OAc to 0.5 M add 2½ volumes of EtOH, and mix thoroughly.

4. Place tubes in −20° C. freezer for 15 minutes.

5. Pellet the RNAs by centrifuging at maximum speed in a microcentrifuge (at least 10,000 rpm) for 15 minutes, preferably at 4° C.

6. Remove the EtOH supernatant, taking care to avoid dislodging the pellets.

7. Dissolve the pellets in 20 μl of Soln. A (hybridization buffer). After adding Soln. A to each pellet, vortex each tube for about 5–10 seconds, then microfuge for a few seconds to collect the liquid at the bottom of the tube.

8. Incubate tubes at 90° C.±5° C. for 3–4 minutes to denature the RNA and aid in its solubilization, then re-vortex and re-microfuge briefly.

9. Incubate tubes, preferably in a 42–45° C. cabinet-type incubator, or submerged in a 45° C. water bath or heat block, for about 2–18 hours to allow hybridization of probe and complementary mRNA in the sample RNA. This step can be conveniently done overnight. However, the hybridization time can be successfully reduced to as little as 2 hours using probe made from the control template included in the kit (Soln. G), hybridized with the control sample RNA (Soln. H, mouse liver RNA). The mRNA being detected in Soln. H is for mouse β-actin, which is a moderately abundant message in mouse liver (Current Protocols in Molecular Biology, 1987). For the initial detection of an mRNA of unknown abundance, we recommend overnight hybridization. Hybridization times may be reduced in subsequent experiments depending on the results (i.e. intensity of signal of the protected fragment). However, for accurate quantitation, the hybridization reaction must go essentially to completion. To eliminate condensation around the tops of the tubes during hybridization, they should be tightly capped and preferable incubated in a cabinet-type incubator. Alternatively, tubes may be submerged in a water bath or water-filled heat block. If incubated in a heat block, condensation will probably result in droplets of water around the top of the tube.

Example 2

At lease 4 α-amylase genes are present in the genome of sugar beet (FIGS. 7A, 7B and 7C). SBAmyA and SBAmyD are expressed in cultured cells and regulated in response to the sugar concentration in the medium. SBAmyB and SBAmyC are expressed in germinating seedlings. Subcloning and characterization of the seedling-expressed α-amylase is described below.

Genes encoding SBAmvB and SBAmyC were identified from a lambda genomic library of sugar beet. Restriction mapping and Southern hybridization of the lambda clones was performed to identify α-amylase gene fragments for subcloning (FIGS. 8A and 8B and 12A, 12B and 12C). Plasmid subclones in pBluescript or pUC vectors were isolated. DNA sequencing was performed by primer walking methods using the ABI 377 Automated DNA Sequencer. Oligonucleotide primers were designed using MacVector software and synthesized by GibcoBRL. Analysis of DNA sequence data was performed using AssemblyLIGN and MacVector software. Sugar beet α-amylase exon sequences were identified based on homology to the mung bean α-amylase gene.

The 5' flanking sequences (promoter and mRNA leader sequences) of SBAmyB (1076 bases) and SBAmyC (525 bases) were amplified by PCR and subcloned into plasmids (FIGS. 10A, 10B and 10C and 13A, 13B and 13C). PCR primers were designed to introduce Pst1 and Nco1 sites into the ends of the fragments (FIGS. 10A and 10B). The Nco1 restriction enzyme site (CC<u>ATG</u>G) was designed to overlap the methionine start codon for translation of the protein-coding region. This simplifies attachment of the promoter to the GUS gene in p2553 (FIG. 15) and to any other target genes that have Nco1 sites at the translation start sties. Pst1 sites were created at the opposite end of the promoter. These PCR products were subcloned into the TA Cloning vector (FIGS. 10A, 10B and 10C) to provide a supply of promoter fragments for future work and into the p2553 Nco-GUS vector (FIGS. 11A and 11B).

Promoter/GUS constructs were made by cutting the PCR products with Nco1 and Pst1 and subcloning directly into p2553 (FIGS. 11A and 11B and 14A and 14B). These constructs were confirmed by DNA sequencing because the PCR amplification may introduce errors onto the sequence. The SBAmyC promoter/GUS construct matches the native promoter sequence perfectly, while the SBAmyB promoter/GUS construct had one mutation 913 bases on the 5' side of the ATG codon. The mutation is not a problem because of the great distance separating it from the ATG codon.

There was little or no homology among the promoter sequences of the SBAmyB, SBAmyC and mung bean α-amylase genes based on Pustel1 matrix analysis (window-10; 65% match) (FIG. 16A, 16B and 16C). This promoter sequence divergence is opposite of the highly conserved exon sequences observed previously (FIGS. 7A, 7B and 7C). This promoter divergence also indicates that each promoter may have distinct functional properties.

Some significant homologies among these promoters may be present, because cis-elements shorter than 10 bases long are not readily detected by Pustel1 matrix analysis. Other than the TATA Box, the sugar beet and mung bean α-amylase promoters do not have the cis-elements identified in the monocot α-amylase promoters.

These promoter constructs are useful for testing the expression of the promoters in transgenic plants using GUS as a reporter gene and for transfer of promoter cassettes into constructs with protein-coding regions of other target genes.

The SBAmyB gene sequence (as depicted in FIGS. 8A, 8B and 9) is provided in SEQ ID NO: 8.

The sequence of the SBAmyB promoter/GUS fusion (as depicted in FIGS. 11A and 11B) is provided in SEQ ID NO: 9.

The SBAmyC gene sequence (as depicted in FIGS. 12A, 12B, 12C, and 12D) is provided in SEQ ID NO: 10.

The sequence of the SBAmyC promoter/GUS fusion (as depicted in FIGS. 14A and 14B) is provided in SEQ ID NO: 11.

While only a few general embodiments of the invention have been shown and described herein, it will become apparent to those skilled in the art that various modifications and changes can be made in the incorporation of the SBAmyA, SBAmyB, SBAmyC or SBAmyD genes of sugar beet into other vectors and incorporation into plants and seed to provide improved physical, biological and chemical properties thereof without departing from the spirit and scope of the present invention. All such modifications and changes coming within the scope of the appended claims are intended to be carried out thereby.

We claim:

1. A method for producing a gene product in an angiosperm host cell, the method comprising,
    cultivating an angiosperm host cell transformed with a vector comprising an SBAmyB promoter (nucleotides 2888 to 4002 of SEQ ID NO: 9) or SBAmyC promoter (nucleotides 2888 to 3446 of SEQ ID NO: 11) fused to a DNA sequence encoding a protein of interest, wherein the cultivating step is performed in a sugar-depleted or sugar-free condition to promote the expression of the protein; and
    recovering the protein.

2. The method of claim 1, wherein the vector comprises an antibiotic resistance gene.

3. The method of claim 1, wherein the vector comprises a reporter gene.

4. The method of claim 3, wherein the reporter gene is a β-glucuronidase (GUS) gene.

5. The method of claim 1, further comprising transforming the host cell prior to the cultivating step.

6. The method of claim 5, wherein the method further comprises constructing the vector prior to the transforming step.

7. The method of claim 1, wherein the protein of interest is fused to SBAmyB, as encoded by exons 1–4 as set forth in bases 1077–1170, 1661–1793, 1898–2706, and 2837–3089, respectively, of SEQ ID No. 8, or SBAmyC, as encoded by exons 1–4 as set forth in bases 526–621, 846–978, 3156–3969, and 3971–4224, respectively, of SEQ ID No. 10.

8. The method of claim 1, wherein the host cell is a rice, barley or wheat cell.

9. The method of claim 8, wherein the host cell is a rice suspension culture cell.

10. The method of claim 1, wherein the host cell is a dicotyledonous plant cell.

* * * * *

SEQUENCE LISTING

```
<160> NUMBER OF SEQ ID NOS: 7

<210> SEQ ID NO 1
<211> LENGTH: 460
<212> TYPE: DNA
<213> ORGANISM: Beta vulgaris
<220> FEATURE:
<221> NAME/KEY: modified_base
<222> LOCATION: (220)
<223> OTHER INFORMATION: a, c, t, g, other or unknown
<220> FEATURE:
<221> NAME/KEY: modified_base
<222> LOCATION: (292)
<223> OTHER INFORMATION: a, c, t, g, other or unknown
<220> FEATURE:
<221> NAME/KEY: modified_base
<222> LOCATION: (433)
<223> OTHER INFORMATION: a, c, t, g, other or unknown

<400> SEQUENCE: 1
aaatcctaga gtacaaaaag agttaataga ttggatgaat tggcttaaaa caagtatagg      60
ctttgatggt tggagattag atttcgttaa aggatattct cctagcataa ctaaattata     120
tatggatcaa actaagccag atttcgccgg ttggagagct atgggactcc attacttatc     180
ttaatggtgc accccgatta caaccaagac ggacatcgan acgagctagc tagatggggt     240
tcaagcctct ggtggaggag ttgttactgc ctttgatttt actacaaaag gnattcttca     300
atatgcagtg caaggacaat ggtggagaat gagagaccct aatggtagac ctagtggact     360
tattggaatt ttaccaaaaa atgctgttac tttccttgat aaccatgata ctggatctag     420
tcaaaaactt tgnccttttc cacctgataa agtcatgcaa                          460

<210> SEQ ID NO 2
<211> LENGTH: 460
<212> TYPE: DNA
<213> ORGANISM: Beta vulgaris
```

<400> SEQUENCE: 2

```
aaatccaagg gtacaaagag aactagttga ttggatgaat tggctgaaga cggaaattgg      60
ttttgacggg tggagatttg attttgtcaa gggatatgct cccagcatta ctaaaattta     120
catggaagag actaggccag attttgcagt tggagagctt tgggattcca ttaattatga     180
tccagacggt aagccagact acaatcaaga cggacctcga aatgaactag ctggatgggt     240
acaagctgca ggtggtggtg ttattgctgc atttgatttc accaccaaag gtgttcttca     300
agctgccgtg caaggagagt ggtggagaat gaaagattct agtggtaggc ctagtgggtt     360
aataggaatt atgcctaaaa atgctgtcac ttttattgat aatcatgaca gtggttccac     420
acaaaggtta tggccttttc ctgcagacaa agtaatgcaa                           460
```

<210> SEQ ID NO 3
<211> LENGTH: 460
<212> TYPE: DNA
<213> ORGANISM: Beta vulgaris

<400> SEQUENCE: 3

```
taatccaaga gtacaaaagg agttagtcga ttggatgaat tggctcaaga cagaaattgg      60
ttttgacgga tggagatttg attttgttaa gggatatgct cctagcatta ccaaaattta     120
catggaaaaa actaggcctg attttgcagt tggagagctt tgggattcca ttacatatga     180
cccggatggt aagccagact ataaccaaga cggacctcga aatgaactag ctggatgggt     240
acaagctgca ggtggtggtg ttattgctgc atttgatttc actaccaaag gtgttcttca     300
agctgctgtt caaggagaat ggtggagaat gaaagattct aatggtaggc ctagtgggtt     360
gataggaatt atgcctaaaa atgctgtcac ttttattgat aatcatgaca ctggttccac     420
acaaaggtta tggccttttc ccgcagacaa agtcatgcaa                           460
```

<210> SEQ ID NO 4
<211> LENGTH: 457
<212> TYPE: DNA
<213> ORGANISM: Beta vulgaris
<220> FEATURE:
<221> NAME/KEY: modified_base
<222> LOCATION: (56)
<223> OTHER INFORMATION: a, c, t, g, other or unknown

<400> SEQUENCE: 4

```
aaatcctaga gtacaaaaag agttaataga ttggatgaat tggcttaaaa caagtntagg      60
ctttgatggt tggagattag atttcgttaa aggatattct cctagcataa ctaaattata     120
tatggatcaa actaagccag atttcgcggt tggagagcta tgggactcca ttacttatct     180
taatggtgca cctgattaca accaagacgg acatcgaaac gagctagcta gatgggttca     240
agcctctggt ggaggagttg ttactgcctt tgattttact acaaaaggaa tacttcaata     300
tgcagtgcaa ggacaatggt ggagaatgaa agaccctaat ggtagaccta gtggacttat     360
tggaattttta ccaaaaaatg ctgttacttt ccttgataac catgatactg gatctagtca     420
aaaactttgg ccttttccac tgataaagt catgcaa                               457
```

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 5
gtatagcttg agcattaccg tcgtgtaatt gcaacacttg gctt                    44

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctcagcttcg gtcccccaag ggaagacca                                     29

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtatgtaagt tgcctttggg tgtaaaattt cttgcatgca                         40
```